POA PRATENSIS

Filed July 20, 1970

INVENTORS
TORAO T. FUCHIGAMI
EUGENE W. MAYER

BY

Strauch, Nolan, Neale, Nies & Kurz
ATTORNEYS

INVENTORS
TORAO T. FUCHIGAMI
EUGENE W. MAYER

BY

Strauch, Nolan, Neale, Nies & Kurz
ATTORNEYS

POA PRATENSIS

Filed July 20, 1970 5 Sheets-Sheet 5

POA PRATENSIS

Filed July 20, 1970 5 Sheets-Sheet 4

POA PRATENSIS

Filed July 20, 1970 5 Sheets-Sheet 5

United States Patent Office

Plant Pat. 3,156

Patented May 9, 1972

3,156

POA PRATENSIS

Torao T. Fuchigami, Long Beach, Calif., and Eugene W. Mayer, Marysville, Ohio, assignors to The O. M. Scott & Sons Company, Marysville, Ohio Filed July 20, 1970, Ser. No. 56,757
Int. Cl. A01h 5/00
U.S. Cl. Plt.—88 1 Claim

ABSTRACT OF THE DISCLOSURE

A variety of *Poa pratensis* characterized by its excellent turf performance and disease resistance, a low growing profile, a deep blue-green color; excellent seed yield, and a favorable response to vertical growth inhibitors of the type described in U.S. Patent No. 3,462,257.

The present invention relates to a new and distinct variety of *Poa pratensis* which has been designated Ba 62–54 Kentucky bluegrass. The foundation plant of the variety was selected from cultivated plots on the west coast by the applicants.

Ba 62–54 Kentucky bluegrass reproduces asexually both apomictically and vegetatively. All asexually reproduced Ba 62–54 offspring appear to show complete conformity with the mother plant.

Ba 62–54 has a number of highly desirable characteristics including a low growing profile, a robust nature, good resistance to turf diseases, a dark, deep, blue-green color, and the capability of producing a dense turf. It also propagates rapidly and is an excellent seed producer. Because of this combination of desirable characteristics, Ba 62–54 Kentucky bluegrass is capable of producing turf of excellent quality.

From the foregoing it will be apparent that the primary object of the present invention resides in the provision of a novel and distinct variety of *Poa pratensis* having the unique combination of characteristics described above. These and other characteristics will be described in detail in the ensuing detailed description and discussion of the invention and, where applicable, are illustrated in the accompanying drawing, in which.

Figure 1:
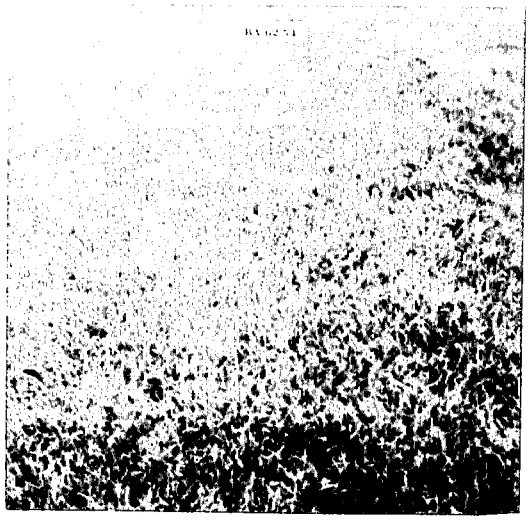
FIG. 1 is a photograph of one-year old Ba 62–54 turf.
Figure 2:
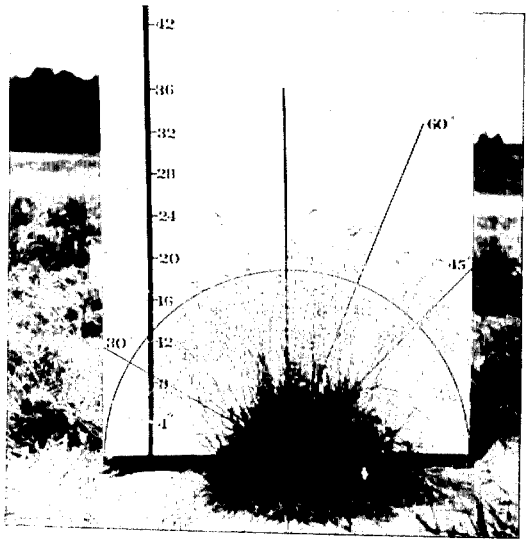
FIG. 2 is a photograph of a mature Ba 62–54 plant grown is a field nursery at Marysville, Ohio.
Figure 3:
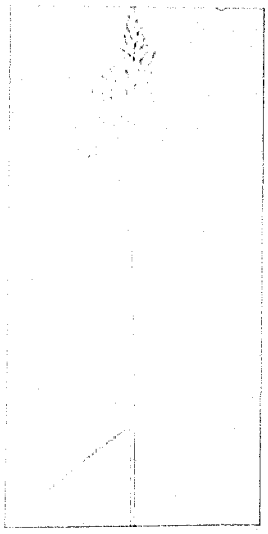
FIG. 3 is a photograph of a mature Ba 62–54 panicle.

Ba 62–54 Kentucky bluegrass (see FIGS. 1 and 2) is characterized by erect tufted culms 50–75 centimeters tall with an average of 55 centimeters when undisturbed by clipping. Blades are soft flat or folded and are mostly 2.5 to 4 mm. wide with an average width in mowed turf in the range of 2.85 mm. to about 3.65 mm. Panicles average 62 to 74 mm. in length, are pyramidal or oblong pyramidal, and range from somewhat contracted to open (see FIG. 3). The lowermost branches are arranged in an average whorl of five, ascending or spreading, and naked below.

Figure 5:
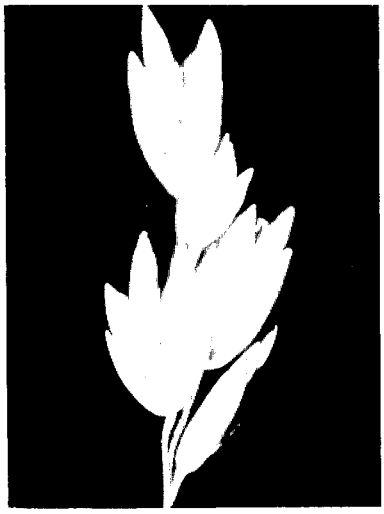
FIG. 5 is a photograph of a mature spikelet of Ba 62–54 grown at Marysville, Ohio.

The spikelet length on the lowest whorl averages 8.53 to 11.27 mm. and that on the third whorl from the bottom averages 8.02 to 10.78 mm. Spikelets are crowded with 1.7 to 3.1 florets (a group of Ba 62–54 florets is shown in FIG. 5). The floret length in the lowest whorl averages 3.67 to 4.53 mm., and the floret length in the third whorl from the bottom averages 3.82 to 4.78 mm.

Lemmas are webbed at the base and pubescent on the lower two-thirds of the keel and the lower half of the marginal nerves. The intermediate nerves are glabrous. The first glume is 3.47 to 4.93 mm. in length, and the second is 3.8 to 5.0 mm. in length.

The foregoing description and measurements are based on plants grown at Marysville, Ohio. Since environmental conditions such as climate and soil influence morphological characteristics to some degree, the morphological characteristics described above may vary.

The morphological characteristics of Ba 62–54 and other commercially available bluegrass varieties are compared in Table I.

TABLE I

Morphological comparison of Ba 62-54 and other bluegrass varieties

| Variety | Mature plant height in centimeters | Panicle whorl branches | Panicle length in mm. | Spikelet length in mm. | | Florets per spikelets | Floret length in mm. | | Glume length in mm. | | Leaf blade width in solid seeded plots in mm.* |
|---|---|---|---|---|---|---|---|---|---|---|---|
| | | | | Lowest whorl | Third whorl | | Lowest whorl | Third whorl | 1st | 2d | |
| Ba 62–54 | 55 | 5 | 62–74 | 8.53 to 11.27 | 8.02 to 10.78 | 1.7–3.1 | 3.67 to 4.53 | 3.82 to 4.78 | 3.47 to 4.93 | 3.8 to 5.0 | 2.85 to 3.65. |
| Newport | 70 | 5 | 71–97 | ---------- | 7.87 to 10.33 | 2–4 | ---------- | 3.90 to 4.81 | 3.42 to 4.98 | 3.56 to 4.64 | 2.02 to 2.72. |
| Merion | 65 | 5 | 72–86 | ---------- | 8.11 to 9.39 | 1.9–3.8 | ---------- | 3.11 to 4.09 | 3.2 to 4.4 | 3.37 to 4.73 | 2.37 to 2.87. |

*Measured one inch from the tip of the boat-shaped blade.

As shown by the foregoing table, the morphological characteristics of Ba 62–54 acord a basis for distinguishing it from other varieties of *Poa pratensis* such as those listed in the table.

Figure 7:
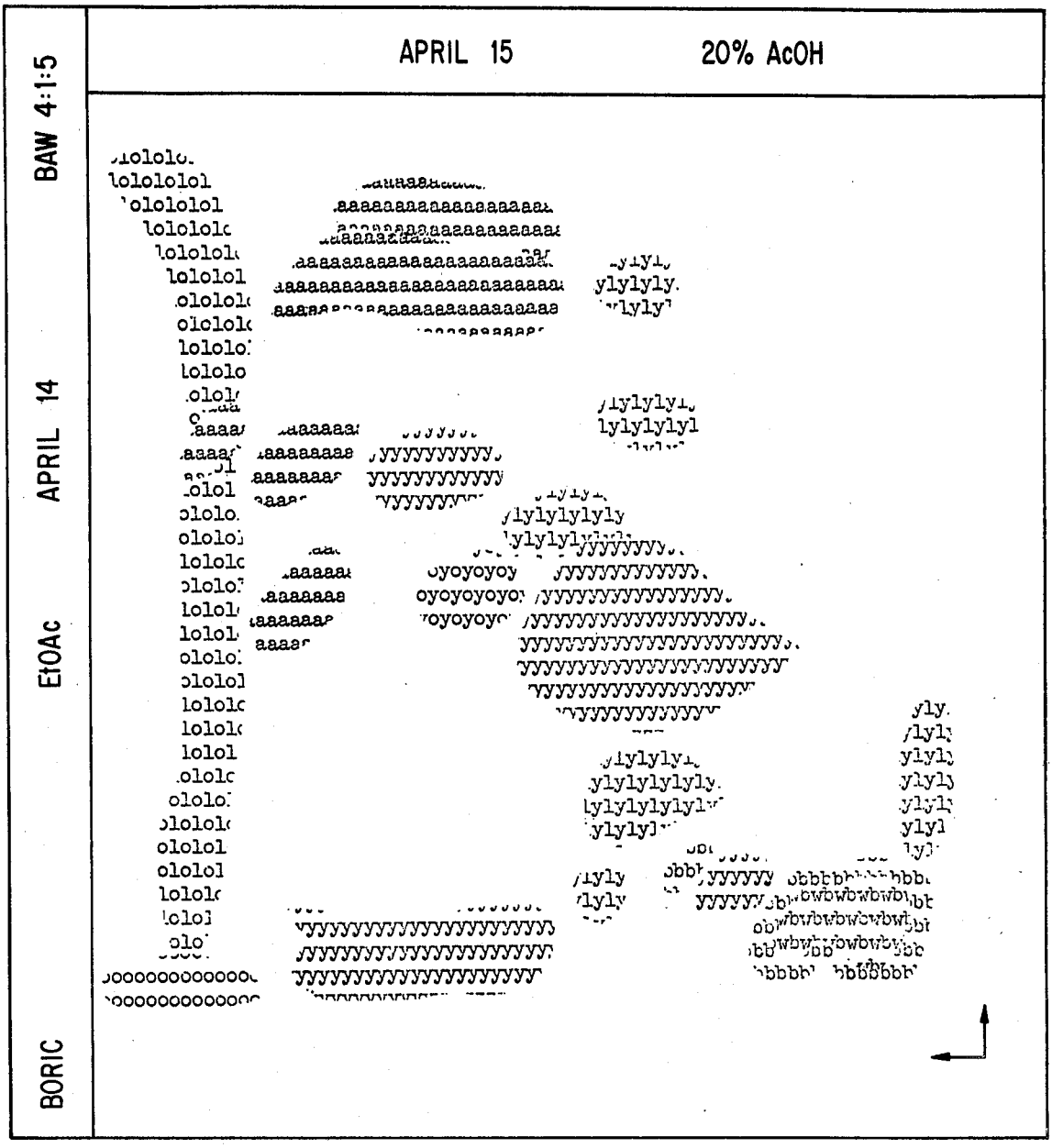
FIGS. 7–9 are representations of thin film chromatographs of extracts obtained from Ba 62–54 leaf clippings.
Figure 8:
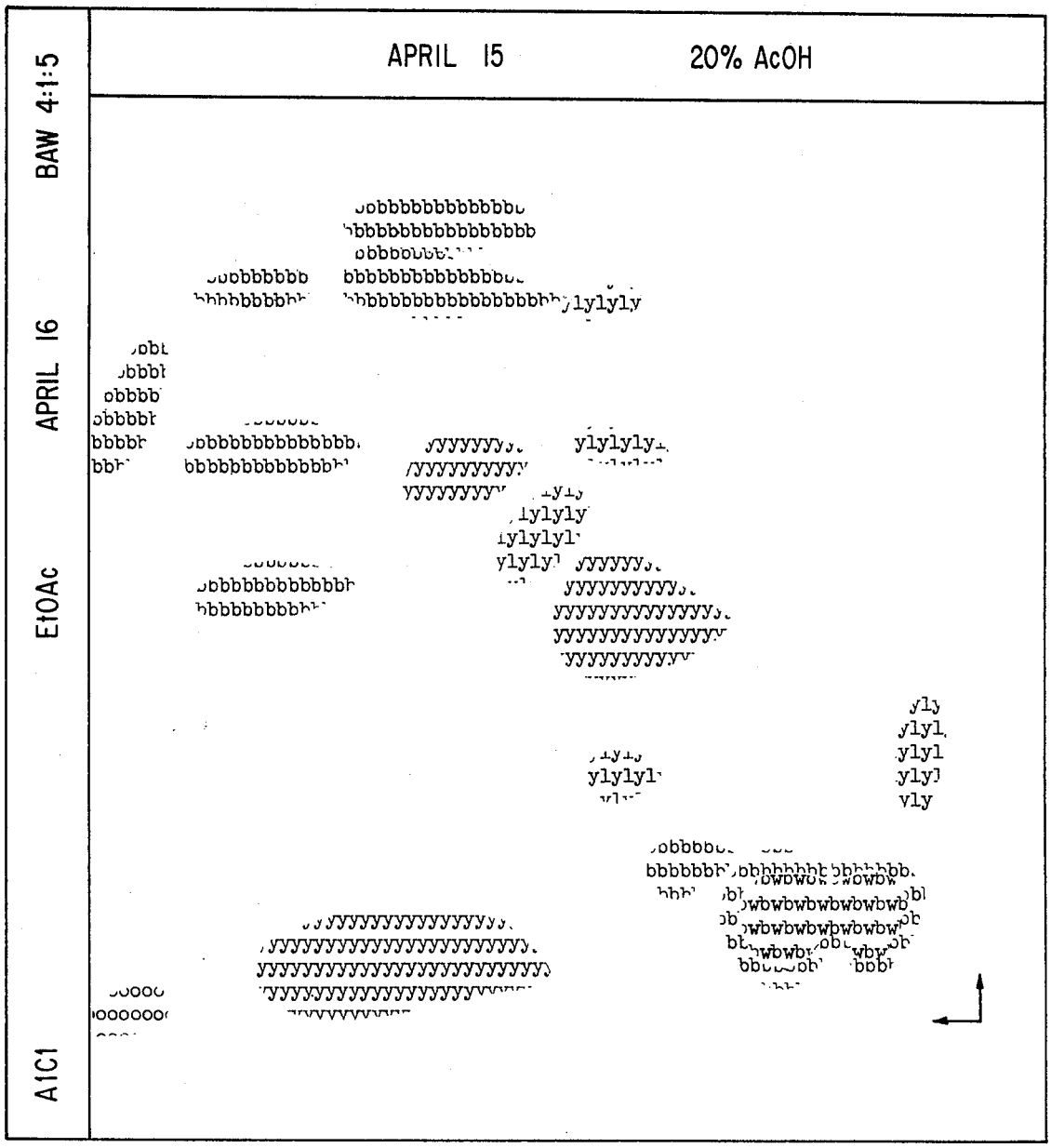
Figure 9:
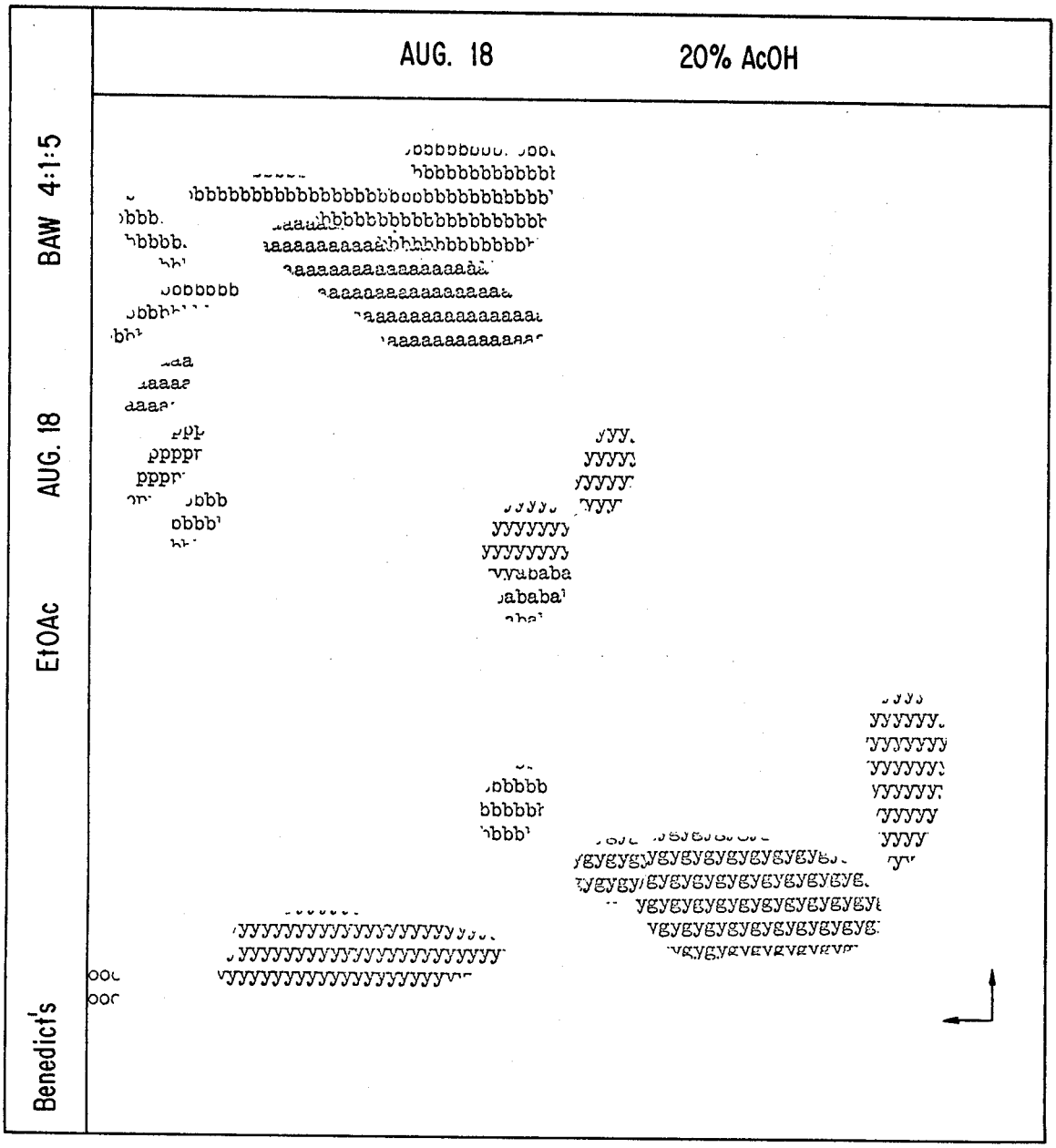

Ba 62–54 Kentucky bluegrass can also be distinguished by a chromatographic analysis of its phenolic constituents. The results of such an analysis are depicted in FIGS. 7–9. In this analysis a sample of Ba 62–54 leaf clippings was extracted with 80% methanol. The extract was concentrated in vacuo and then extracted with petroleum ether to remove chlorophylls, carotenoids, and other fat soluble material. After further concentration in vacuo this extract was saturated with sodium chloride and extracted with ethyl acetate giving a polyphenol fraction designated Ba 62–54 EtOAc.

This fraction was chromatographed by the two-dimensional thin layer technique. More particularly, the fraction was spotted on 20 x 20 cm. plates coated with Avicel microcrystalline cellulose, which were developed first in butanol-acetic acid-water (4:1:5) and after thorough drying then developed in 20% acetic acid and again dried. The dried two-dimensional chromatograms were sprayed with a 1% diphenylboric acid ethanolamine complex in methanol, 1% aluminum chloride in methanol, and Benedict's reagent.

When the sprayed chromatograms were viewed under ultraviolet light (350 millimicron) the patterns shown in FIGS. 7–9 were observed. In these figures the following code is employed:

| | |
|---|---|
| a=aqua | o=orange |
| ab=absorbent spot | lo=light orange |
| b=blue | p=purple |
| bw=blue-white | y=yellow |
| by=bluish-yellow | ly=light yellow |
| gy=greenish-yellow | yo=yellowish-orange |

Mowed plots of Ba 62–54 Kentucky bluegrass have been evaluated at Marysville, Ohio; Long Beach, Calif.; and Washington, D.C. These evaluations confirmed that Ba 62–54 has many significant desirable characteristics which enable it to provide good performance as described below.

Turf density measurements were made throughout the year and at different heights of cut to provide information on the growth habits of the grass. The data collected showed that two, three, and four year old Ba 62–54 turf maintained excellent density throughout the growing season at all heights of cut, even under unfavorable growing conditions.

More particularly, the data in Table II below shows that turf density of Ba 62–54 Kentucky bluegrass in Marysville, Ohio, at two low heights of cut was excellent and superior to that of Park and Common Kentucky from spring through autumn. Density ratings of Ba 62–54 Kentucky bluegrass at Washington, D.C. were equal to or higher than those of other standard varieties during every month in which data was collected (see Table III). The difference is especially evident during the stress months for bluegrasses (July and August) when climatical conditions are normally very hot and dry. Plots of Ba 62–54 at Long Beach, Calif. also had good density (see Table IV). Excellent density ratings at all of the above locations is indicative of the broad genetic environmental adaptability possessed by Ba 62–54 Kentucky bluegrass.

TABLE II

[Turf density comparisons of Ba 62–54 and other bluegrass varieties at 1 inch and ½ inch heights of cut at Marysville, Ohio]

| Variety | Rating, percent | | | | | |
|---|---|---|---|---|---|---|
| | May | | July | | October | |
| | 1" | ½" | 1" | ½" | 1" | ½" |
| Ba 62–54 | 95 | 90 | 100 | 95 | 100 | 100 |
| Park | 90 | 80 | 90 | 90 | 95 | 90 |
| Common Kentucky | 80 | 65 | 80 | 70 | 90 | 80 |
| Merion | 95 | 90 | 100 | 95 | 100 | 100 |

Ranking scale: Number indicates percent coverage of the plot by desirable turf.

TABLE III

[Turf density comparisons of Ba 62–54 and other bluegrass varieties at a 2 inch height of cut at Washington, D.C.]

| Variety | Rating, percent | | | |
|---|---|---|---|---|
| | April | June | August | October |
| Ba 62–54 | 65 | 90 | 75 | 100 |
| Newport | 80 | 50 | 50 | 45 |
| Common Kentucky | 85 | 45 | 45 | 70 |
| Merion | 87 | 85 | 30 | 35 |

Ranking scale: Number indicates percent coverage of the plot by desirable turf.

TABLE IV

[Turf density comparisons of Ba 62–54 and other bluegrass varieties at a 1½ inch height of cut at Long Beach, California]

| Variety | Rating, percent | | | | | |
|---|---|---|---|---|---|---|
| | Jan. | Mar. | May | June | Sept. | Nov. |
| Ba 62–54 | 95 | 100 | 90 | 85 | 100 | 100 |
| Newport | 95 | 95 | 80 | 65 | 80 | 90 |
| Merion | 80 | 85 | 60 | 75 | 80 | 90 |
| Park | 95 | 100 | 90 | 90 | 80 | 90 |

Ranking scale: Number indicates percent coverage of the plot by desirable turf.

The speed and ability of a variety to spread and fill in a plot after sprigging constitute a good measure of the turf vigor and persistence possessed by the variety. One month after sprigging plant material at replicated randomized plots in Washington, D.C. Ba 62–54 was giving a more rapid rate of spread. Two months after sprigging Ba 62–54 covered 80% of the plot compared to Merion, which only covered a little over half of the plot area (see Table V). This demonstrates the robust nature and the spreading ability of Ba 62–54.

TABLE V

[Rate of spread and turf coverage comparisons between Ba 62–54 and Merion bluegrasses at Washington, D.C.]

| Variety | Rate of spread one month after sprigging | Turf coverage two months after sprigging, percent |
|---|---|---|
| Ba 62–54 | 3 | 80 |
| Merion | 1 | 55 |

Ranking scale: 1=Slow rate of spread; 3=fast rate of spread.

NOTE.—Number indicates percent of coverage of plot by desirable turf.

Disease resistance is a highly significant and desirable characteristic that is necessary to the maintenance of good quality turf. Ba 62–54 Kentucky bluegrass has provided good resistance to many major types of turf diseases in varied geographical locations. This again demonstrates the broad genetic adaptability of this grass.

With continued reference to the disease resistance of Ba 62–54, the spring season of each year is quite favorable to the development and infestation of bluegrass by Helminthosporium spp. (leaf spot). Therefore, the incidence of leaf spot is normally at its peak at this time of the year; and evaluation of variety resistance at this time is accordingly highly significant. A comparison of data for the month of May in three consecutive years taken from the same plots and for the same varieties showed that the severity of leaf spot increased each year in all plots [1] but not to the same extent. Ba 62–54 was comparable to Merion [2] in resistance each consecutive year and was significantly more resistant to the disease than Park and Common Kentucky. (See Table VI.) Leaf spot damage was minimal to the Ba 62–54 and Merion plots. However, other common turf varieties were severely damaged and thinned. Data from Washington, D.C. turf plots also indicated that Ba 62–54 has resistance comparable to that of Merion. (See Table VII.)

TABLE VI

[Comparison of the susceptibility of Ba 62–54 and other bluegrass varieties to the causal organism Helminthosporium spp. in May for three consecutive years at Marysville, Ohio.]

| Variety | Percent | | |
|---|---|---|---|
| | First year | Second year | Third year |
| Ba 62–54 | 15 | 23 | 30 |
| Park | 50 | 40 | 80 |
| Common Kentucky | 50 | 40 | 83 |
| Merion | 25 | 25 | 35 |

Ranking scale: Number indicates percent of disease incidence in plot.

[1] An increase in the incidence of leaf spot can be expected as turf becomes older.

[2] Merion is recognized as having good resistance to leaf spot.

TABLE VII

[Comparison of the susceptibility of Ba 62–54 and other bluegrass varieties to the causal organism Helminthosporium spp. in May at Washington, D.C.]

| Variety: | Ranking scale, percent |
|---|---|
| Ba 62–54 | 23 |
| Newport | 33 |
| Common Kentucky | 80 |
| Merion | 13 |

Ranking scale: Number indicates percent of disease incidence in plot.

On the west coast *Puccinia graminis* (rust) incidence is normally high on bluegrass turf as ecological conditions in this area are most ideal for this particular disease. Turf can be severely damaged or its aesthetic value decreased when rust incidence is at epidemic proportions. Ba 62–54 bluegrass is significantly more resistant to rust than Merion as shown by the data in Table VIII.

TABLE VIII

[Comparison of the susceptibility of Ba 62-54 and other bluegrass varieties to the causal organism *Puccinia graminis* at Long Beach, Calif.]

| Variety | Percent | |
|---|---|---|
| | September, first year | August, second year |
| Ba 62-54 | 25 | 10 |
| Newport | 10 | 20 |
| Merion | 50 | 40 |

Ranking scale: Number indicates percent of disease incidence in plot

Figure 4:
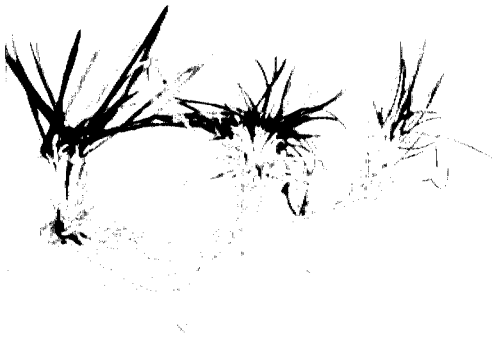
FIG. 4 is a photograph of Ba 62–54 roots and rhizomes.

Ba 62–54 is also characterized by vigorous rhizome formation (see FIG. 4). The variety is comparable in this respect to Windsor bluegrass.

Another novel characteristic of Ba 62–54 Kentucky blue-grass is its favorable response to vertical growth inhibitors such as 6-azauracil.[3] As shown by the data in Table IX, the application of 6-azauracil at the rate of two pounds per acre to Ba 62–54 turf in good growing condition produced a 40% reduction in vertical growth and a 70% reduction of fresh weight material 28 days after treatment without severe injury to the turf. This genetic characteristic may be useful in reducing mowing frequencies at peak growing times of the year, and may also assist in variety identification.

TABLE IX

[Response of Ba 62-54 and Merion bluegrass to 6-azauracil at 2 lbs./acre 28 days after treatment]

| Variety | Inhibition, percent | Injury, percent | Turf quality | Fresh weight reduction percent |
|---|---|---|---|---|
| Ba 62-54 | 40 | 0 | 3 | 70 |
| Merion | 5 | 0 | 3 | 44 |

Ranking scale:
Inhibition=Number indicates percent inhibition to desirable turf.
Injury=Number indicates percent injury to desirable turf.
Turf quality:
1–3 excellent.
4–7 fair.
8–10 poor.
Fresh weight reduction=Number indicates percent fresh weight reduction.

Ba 62–54 Kentucky bluegrass is a very prolific and heavy seed producer both at Marysville, Ohio and Salem, Oreg.

Yields of 38 grams of seed per plant were obtained at Salem compared to 11 grams of seed per plant for Windsor Kentucky bluegrass.

The initial heading date of Ba 62–54 Kentucky bluegrass was 14 days later than Windsor Kentucky bluegrass. The Ba 62–54 reached the point where 50% of the plants were headed seven days later than Windsor, which indicates that Ba 62–54 will head out more rapidly once initial heading occurs. The first anthesis date was approximately the same as for Windsor; however, harvest for Ba 62–54 was 18 days earlier than Windsor because of faster maturity (see Table X).

TABLE X

[Comparison dates of heading, anthesis, harvest and seed yields of Ba 62-54 and Windsor bluegrasses at Salem, Oregon]

| Variety | Heading date | | Anthesis date | | Harvest date | Seed yield/plant, gms. |
|---|---|---|---|---|---|---|
| | First | 50% | First | 50% | | |
| Ba 62-54 | 5-3 | 5-6 | 5-24 | 5-27 | 7-5 | 38 |
| Windsor | 4-19 | 4-29 | 5-22 | 5-27 | 7-23 | 11 |

Ba 62–54 Kentucky bluegrass has a deep, blue-green color. It is very pleasing to the eye and has excellent aesthetic value.

[3] The use of 6-azauracil and related compounds as vertical plant growth inhibitors is disclosed in detail in United States Patent No. 3,462,257 to which the reader may refer, if desired.

Ba 62–54 had a darker green color on the west coast throughout the year than other standard turfgrass varieties (see Table XI). This was especially evident during the winter months with Ba 62–54 maintaining a greener color. This is a very desirable characteristic especially on the west coast, which has mild winters, making it possible to have a green lawn the entire year.

TABLE XI

[Turf color comparisons of Ba 62-54 and other bluegrass varieties at Long Beach, California]

| Variety | Jan. | Mar. | May | June | Aug. | Sept. | Dec. |
|---|---|---|---|---|---|---|---|
| Ba 62-54 | 8.7 | 9 | 10 | 10 | 10 | 10 | 9 |
| Newport | 8.3 | 8.5 | 9 | 10 | 9.3 | 9 | 9 |
| Merion | 5 | 7 | 9 | 9 | 8.5 | 9 | 6 |
| Park | 6.5 | 6.5 | 7 | 7 | 6 | 6 | 5 |

Ranking scale: 10=darkest green; 1=brown color or straw color.

In the northern and eastern areas where winters are extremely cold, Ba 62–54 does not become as straw colored as other standard varieties. Therefore, even in these areas, it has a more appealing winter color.

The various turf and turfgrass characteristics described above are all taken into account in determining what is known as a turf quality rating. Great significance is attached to this rating because it is indicative of the general appearance, uniformity, and aesthetic value of a turf. Also, as all of the performance characteristics of the grass are taken into consideration, a good turf rating is an indication that the grass is free of disease, has good color, density, and uniformity, and an acceptable texture, and that it is pleasing to walk on.

The turf quality of two, three, and four year old Ba 62–54 turf has been found to be excellent. In fact, the quality of four year old Ba 62–54 turf was significantly better than that of two year old turf of other varieties in plots in Marysville, Ohio (see Table XII). This is significant because older turf is usually lower in quality than younger or juvenile turf.

On the west coast, Ba 62–54 also had better turf quality ratings throughout the year than the standard varieties as shown by Table XIII. Excellent turf quality ratings throughout the year and at different geographical locations again reflect the wide genetic base of Ba 62–54.

TABLE XII

[Turf quality comparisons of Ba 62-54 and other bluegrass varieties in August for three consecutive years at Marysville, Ohio]

| Variety | 2 yr. old turf | 3 yr. old turf | 4 yr. old turf |
|---|---|---|---|
| Ba 62-54 | 4 | 3 | 3.5 |
| Park | 2 | 1.5 | 2 |
| Common Kentucky | 2 | 1.5 | 2 |
| Merion | 3 | 3 | 3.5 |

Ranking scale: 4=excellent turf quality; 1=poor turf quality.

TABLE XIII

[Turf quality comparisons of Ba 62-54 and other bluegrass varieties at Long Beach, California]

| Variety | July | September | November | December |
|---|---|---|---|---|
| Ba 62-54 | 4 | 4 | 3 | 3 |
| Park | 1 | 1 | 2 | 1 |
| Newport | 2 | 3 | 3 | 3 |
| Merion | 2 | 2 | 2 | 1.5 |

Ranking scale: 4=excellent turf quality; 1=poor turf quality.

Figure 6:
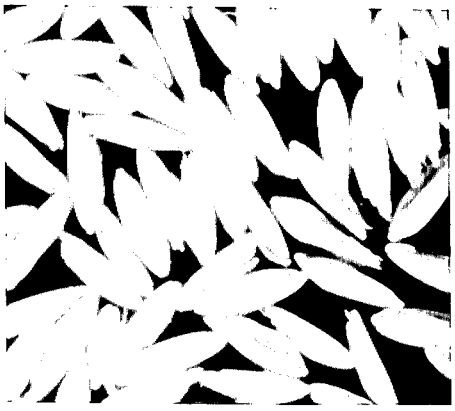
FIG. 6 is a photograph of Ba 62–54 seed produced at Salem, Oreg.

The size and weight of Ba 62–54 seed is also unique. Most bluegrass varieties have from one million, three hundred thousand to two million seeds per pound. However, Ba 62–54 seed (see FIG. 6) is much heavier than the seed of standard varieties so there are less than a million seeds per pound. (See Table XIV.)

TABLE XIV

[Comparison of Ba 62-54 and other bluegrass varieties as to the number of seeds produced per pound in the Pacific Northwest]

| Variety | Number of seeds per pound | Moisture percentage of each seed |
|---|---|---|
| Ba 62-54 | 898,012 to 931,608 | 6.3 |
| Newport | 1,154,522 to 1,216,266 | 6.9 |
| Merion | 1,813,730 to 1,869,118 | 6.9 |
| Park | 1,179,492 to 1,220,352 | 6.7 |
| Delta | 1,216,720 to 1,277,556 | 7.3 |
| Windsor | 1,370,626 to 1,418,750 | 7.0 |

NOTE.—Number of seeds per pound were determined by counting one gram lots using an electric seed counter.

Ba 62–54 seed also has a rapid rate of germination and excellent seedling vigor. For example, under good germinating conditions (81° F. for 8 hours with light alternated with 16 hours darkness at 60° F.), Ba 62–54 germinated significantly faster within the first 14 days than most standard varieties (see Table XV). Because of this fast germination rate, critical establishment time is significantly reduced, providing the seedlings with a better chance of survival.

TABLE XV

[Seed germination percentage rates of Ba 62-54 and other bluegrass varieties for 7, 14, 21 and 28 days]

| Variety | Percent | | | |
|---|---|---|---|---|
| | 7 days | 14 days | 21 days | 28 days |
| Ba 62-54 | 41 | 92.6 | 98.6 | 99.6 |
| Newport | 3 | 77 | 89 | 93 |
| Merion | 3.3 | 71 | 91.6 | 92.6 |
| Windsor | 22.3 | 80.6 | 92.3 | 93 |

Ranking scale: Number indicates average percentage of seeds that germinated. Seeds were germinated in a germination chamber at 81° F. with 8 hours of light alternated with 16 hours of darkness at 60° F.

The invention may be embodied in other specific forms without departing from the spirit or essential characteristics thereof. The present invention is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A variety of *Poa pratensis* substantially as shown and described herein.

No references cited.

ROBERT E. BAGWILL, Primary Examiner

UNITED STATES PATENT OFFICE

CERTIFICATE OF CORRECTION

Patent No. Plant Patent No. 3,156 Dated May 9, 1972

Inventor(s) Torao T. Fuchigami and Eugene W. Mayer

It is certified that error appears in the above-identified patent and that said Letters Patent are hereby corrected as shown below:

Column 2, line 42, change "acord" to --afford--.

Column 3, (in table IV) Merion Jan. change "80" to --90--.

Column 4, line 22, "Helmint hosporium spp." should be underlined or in italics.

Signed and sealed this 12th day of December 1972.

(SEAL)
Attest:

EDWARD M.FLETCHER,JR.
Attesting Officer

ROBERT GOTTSCHALK
Commissioner of Patents